(12) United States Patent
Kang et al.

(10) Patent No.: US 7,329,628 B2
(45) Date of Patent: Feb. 12, 2008

(54) METHOD FOR PREPARING CATALYSTS FOR PARTIAL OXIDATION OF PROPYLENE AND ISO-BUTYLENE

(75) Inventors: Jung-Hwa Kang, Seoul (KR); Won-Ho Lee, Daejeon (KR); Min-Ho Kil, Busan (KR)

(73) Assignee: LG Chem, Ltd. (KR)

( * ) Notice: Subject to any disclaimer, the term of this patent is extended or adjusted under 35 U.S.C. 154(b) by 198 days.

(21) Appl. No.: 10/509,645

(22) PCT Filed: Mar. 19, 2004

(86) PCT No.: PCT/KR2004/000600

§ 371 (c)(1),
(2), (4) Date: Sep. 29, 2004

(87) PCT Pub. No.: WO2004/085060

PCT Pub. Date: Oct. 7, 2004

(65) Prior Publication Data

US 2005/0165252 A1    Jul. 28, 2005

(30) Foreign Application Priority Data

Mar. 26, 2003    (KR) .................. 10-2003-0018917

(51) Int. Cl.
    *B01J 21/00*    (2006.01)
    *B01J 23/00*    (2006.01)
(52) U.S. Cl. ............... 502/311; 502/248; 502/255; 502/312; 502/313; 502/314; 502/315; 502/316
(58) Field of Classification Search ........... 502/248, 502/255, 311, 313–316, 312
    See application file for complete search history.

(56) References Cited

U.S. PATENT DOCUMENTS

| | | | | |
|---|---|---|---|---|
| 3,992,419 A | * | 11/1976 | Otaki et al. .............. 549/258 |
| 4,298,763 A | * | 11/1981 | Engelbach et al. ......... 568/479 |
| 4,321,160 A | * | 3/1982 | Farrington et al. ......... 502/209 |
| 4,382,880 A | * | 5/1983 | Derrien .................. 502/313 |
| 4,388,226 A | * | 6/1983 | Derrien et al. ............ 502/308 |
| 4,418,007 A | * | 11/1983 | Derrien .................. 502/312 |
| 4,837,191 A | * | 6/1989 | Glaeser et al. ............ 502/202 |
| 5,144,090 A | | 9/1992 | Honda et al. |
| 5,364,522 A | * | 11/1994 | Wang ........................ 205/50 |
| 5,602,280 A | | 2/1997 | Nagai et al. |
| 5,728,894 A | * | 3/1998 | Nagano et al. ............. 568/479 |
| 6,525,217 B1 | * | 2/2003 | Unverricht et al. ......... 562/544 |
| 6,881,702 B2 | * | 4/2005 | Arnold et al. ............. 502/311 |

FOREIGN PATENT DOCUMENTS

| | | |
|---|---|---|
| CN | 1210511 A | 3/1999 |
| CN | 1283604 | 2/2001 |
| CN | 1379759 | 11/2002 |
| EP | 0293859 | 12/1988 |
| JP | 4412129 | 6/1969 |
| JP | 4911371 | 1/1974 |
| JP | 5025914 | 3/1975 |
| JP | 5285091 | 7/1977 |
| JP | 11057476 | 3/1999 |
| JP | 2002316047 | 10/2002 |
| KR | 19980073604 | 11/1998 |
| KR | 19980073605 | 11/1998 |

OTHER PUBLICATIONS

Chinese Patent Office, Chinese Office Action w/English Abstract, dated Sep. 8, 2006.
Written Opinion dated Mar. 19, 2004 for Application No. PCT/KR2004/000600.
International Search Report dated Jul 6, 2004 for Application No. PCT/KR2004/000600 (All references cited in Search Report are listed above).
Chinese Office Action dated Mar. 30, 2007 for Application No. 200480000107.0 (All references cited in Office Action are listed above).

* cited by examiner

*Primary Examiner*—Cam N. Nguyen
(74) *Attorney, Agent, or Firm*—Cantor Colburn LLP

(57) ABSTRACT

The present invention relates to a process for preparing a catalyst for partial oxidation of propylene and iso-butylene, and more particularly to a process for preparing a catalyst for partial oxidation of propylene and iso-butylene that can stably prepare a catalyst that shows high activity for conversion of propylene and iso-butylene to obtain acrolein and methacrolein with a high yield, by dissolving salts of metals acting as a catalyst in a nitric acid aqueous solution or in an organic acid solution to prepare a catalyst suspension, drying the catalyst solution in a microwave oven, and then pulverizing and molding the dried catalyst, and calcining the catalyst.

5 Claims, No Drawings

METHOD FOR PREPARING CATALYSTS FOR PARTIAL OXIDATION OF PROPYLENE AND ISO-BUTYLENE

TECHNICAL FIELD

The present invention relates to a process for preparing a catalyst for partial oxidation of propylene and iso-butylene, and more particularly to a process for preparing a catalyst for partial oxidation of propylene and iso-butylene that can stably prepare a catalyst that shows high activity for conversion of propylene and iso-butylene to obtain acrolein and methacrolein with a high yield.

BACKGROUND ART

Partial oxidation employing a complex oxide of transition metals as a catalyst is industrially very important, because it produces intermediates of high value for chemical engineering such as aldehydes, organic acids, epoxy compounds, nitrile compounds, and the like.

In partial oxidation, complete oxidation that produces carbon dioxide and water is inhibited, and it is important how selectively a desired partial oxidation product is produced. Thus, a catalyst used in partial oxidation should be able to inhibit the generation of carbon monoxide or carbon dioxide, and simultaneously, it should have high activity so that it may be economically valuable. Generally, partial oxidation employs a metal, a single metal oxide, a complex metal oxide, or the like as a catalyst, and particularly a complex metal oxide is predominantly employed.

Since partial oxidation is generally an exothermic reaction, and selectivity of the partial oxidation is sensitive to reaction temperature, a complex oxide catalyst that shows activity even at a low temperature is required. Catalysts for partial oxidation are widely employed in various fields.

In general, among the complex oxide catalysts, acrylic acid and methacrylic acid are prepared by gas phase contact oxidation of acrolein and methacrolein that are produced by partial oxidation of propylene and iso-butylene. This preparation process is carried out under as low an oxygen concentration and as low a reaction temperature as possible, so that combustion due to an increase in oxygen concentration of reactants is avoided, overreaction is prevented, and selectivity of acrolein or methacrolein is not deteriorated. Additionally, a catalyst that shows high activity at a low reaction temperature has higher inactivation resistance than a catalyst showing comparatively low activity. Therefore, many studies regarding a catalyst for partial oxidation of propylene and iso-butylene have been undertaken.

Thus far, in order to effectively prepare acrylic acid or methacrylic acid by gas-phase contact oxidation of acrolein or methacrolein, various methods have been suggested.

As examples, Japanese Laid-Open Patent Publication Sho 44-12129 discloses a catalyst consisting of molybdenum, vanadium, and tungsten; Japanese Laid-Open Patent Publication Sho 49-11371 discloses a catalyst consisting of molybdenum, vanadium, copper, tungsten, and chromium; Japanese Laid-Open Patent Publication Sho 50-25914 discloses a catalyst consisting of molybdenum and vanadium; and Japanese Laid-Open Patent Publication Sho 52-85091 discloses a catalyst consisting of one or more components selected from the group consisting of molybdenum, vanadium, copper, antimony, and germanium.

Also, European Patent No. 023,859 discloses that acrolein conversion rate and acrylic acid yield are varied according to methods for molding a catalyst when the components and compositional ratio of a catalyst is identical, and also discloses a process for preparing a catalyst having high acrylic acid yield. In addition, Korean Patent Application No. 1998-073605 discloses a process for preparing a catalyst suspension by controlling the weight of water based on total weight of metal salts, and Korean Patent Application No. 1998-073604 discloses that catalyst activities are varied according to particle sizes.

However, these methods have problems in that a lot of time and cost are required for drying due to the use of a large amount of water when preparing a catalyst, and the control of catalyst properties is difficult.

For improvement of the drying method, Japanese Patent No. 2002-316047 discloses a method using a microwave when preparing a catalyst for oxidation of propane. However, because this method uses water when preparing a catalyst for oxidation of propylene and iso-butylene, a phase separation occurs due to precipitation of metal components when preparing a catalyst slurry. If a drying process using a microwave is used for a layer-separated slurry, catalyst activity is deteriorated. The present invention employs an organic acid such as nitric acid and citric acid instead of the layer-separated slurry to prepare a completely dissolved slurry, and improves catalyst activity by drying the thus-prepared slurry using a microwave.

[Technical Problem]

In order to solve the problems of the prior art, it is an object of the present invention to provide a process for preparing a catalyst for partial oxidation of propylene and iso-butylene, which can reduce time and cost required for drying and improve physical properties of the catalyst.

It is another object of the present invention to provide a catalyst for partial oxidation of propylene and iso-butylene, which shows high activity for conversion of propylene and iso-butylene, shows high selectivity for partial oxidation, and can obtain acrolein and methacrolein with a high yield.

[Technical Solution]

In order to achieve these objects, the present invention provide a process for preparing a catalyst for partial oxidation of propylene and iso-butylene represented by the following Chemical Formula 1, which process comprises the steps of:

a) dissolving a metal salt comprising
  i) a molybdenum salt,
  ii) a bismuth salt,
  iii) an iron salt,
  iv) one or more kinds of salts of metals selected from the group consisting of cobalt, tungsten, vanadium, antimony, and nickel, and
  v) one or more kinds of salts of metals selected from the group consisting of potassium, rubidium, and cesium,
in a nitric acid solution or in an organic acid solution to prepare a catalyst suspension;

b) drying the catalyst suspension of step a) in a microwave oven;

c) pulverizing and molding the dried catalyst of step b); and d) calcining the catalyst powder obtained in step c)

$$Mo_a Bi_b Fe_c X_d Y_e O_f \qquad \text{[Chemical Formula 1]}$$

(wherein X is cobalt, tungsten, vanadium, antimony, or nickel,

Y is potassium, rubidium, or cesium, each of a, b, c, d, and e represents the atomic mole ratio of each metal, and when a is 12, b is 0.5~2, c is 0.5~2, d is 3~8, and e is 0.005~0.2, and f is determined according to the oxidation state of each metal.)

The present invention also provides a catalyst for partial oxidation of propylene and isobutylene represented by the above Chemical Formula 1, which is prepared by dissolving a metal salt comprising a molybdenum salt; a bismuth salt; an iron salt; one or more kinds of salts of metals selected from the group consisting of cobalt, tungsten, vanadium, antimony, and nickel; one or more kinds of salts of metals selected from the group consisting of potassium, rubidium, and cesium in a nitric acid aqueous solution or in an organic acid solution to prepare a catalyst suspension, drying the catalyst suspension in a microwave oven, pulverizing the dried catalyst, and calcining the pulverized catalyst powder.

[Advantageous Effects]

According to the present invention, time and cost required for drying when preparing a catalyst can be reduced, physical properties of a catalyst can be improved, and a catalyst for partial oxidation of propylene and isobutylene, which shows higher propylene and isobutylene conversion rates and high selectivity for partial oxidation, and can obtain acrolein and methacrolein with a high yield, can be stably prepared.

BEST MODE

The present invention will now be explained in detail.

The inventors, during studies on a process for preparing a catalyst for partial oxidation of propylene and iso-butylene capable of reducing time and cost required for drying and improving physical properties of the catalyst, prepared a catalyst by drying a catalyst suspension prepared by dissolving salts of metals acting as a catalyst in a nitric acid aqueous solution or in an organic acid solution in a microwave oven, pulverizing the catalyst suspension, and molding and calcining the pulverized catalyst powder. As a result, it has been discovered that time and cost required for drying when preparing the catalyst can be reduced, physical properties of the catalyst can be improved, the catalyst shows higher conversion of propylene and iso-butylene and high selectivity for partial oxidation, and acrolein and methacrolein can be obtained with a high yield.

The catalyst for partial oxidation of propylene and iso-butylene of the present invention is prepared by drying a catalyst suspension prepared by dissolving salts of metals acting as a catalyst in a nitric acid aqueous solution or in an organic acid solution in a microwave oven, pulverizing the dried catalyst, and calcining the pulverized catalyst powder.

The process for preparing a catalyst for partial oxidation of propylene and iso-butylene of the present invention will be explained in more detail.

a) Preparation of a Catalyst Suspension

In this step, salts of metals acting as a catalyst for partially oxidizing propylene and iso-butylene into acrolein are dissolved in a nitric acid aqueous solution or in an organic acid solution to prepare a catalyst suspension.

As the metal, molybdenum, bismuth, iron, cobalt, tungsten, vanadium, antimony, nickel, potassium, rubidium, or cesium can be used.

When the metal salts are dissolved in a nitric acid aqueous solution or in an organic acid solution, they interact to obtain a completely dissolved suspension.

b) Drying

The thus-prepared catalyst suspension is dried in a microwave oven.

The microwave oven is not specifically limited.

The drying is preferably carried out at a wavelength of the microwave oven of 600 MHz to 2.5 GHz, and more preferably 600 MHz to 1 GHz. If the wavelength of the microwave oven is less than 600 MHz, drying time increases, and if the wavelength exceeds 2.5 GHz, particle size increases.

The drying is preferably carried out for 30 seconds to 5 minutes for 10 ml of a catalyst suspension, and more preferably for 30 seconds to 2 minutes.

The drying in a microwave oven can reduce time required for drying to approximately 1/20 compared with conventional catalyst preparation, and thus decrease cost.

c) Pulverization

In this step, the catalyst dried in the microwave oven is pulverized.

The pulverization is preferably carried out such that a particle size becomes 100 mesh or less. The pulverized size is not specifically limited.

d) Calcination

In this step, the pulverized catalyst is molded and calcined. The molding can be carried out by common methods such as extrusion, inert support coating, and the like.

The calcination is preferably carried out at 350 to 450° C. for 4 to 6 hours, and more preferably at 400° C. for 5 hours. Also, the calcining is preferably carried out in an air atmosphere.

The thus-prepared catalyst has a surface area of twice to three times of that of a catalyst prepared by the conventional method, and it preferably has a surface area of 10 to 20 m$^2$/g. Such an increase in a catalyst surface area increases activity of the catalyst and reduces the amount of the catalyst to be used.

And, when the catalyst is commercially employed, it can be molded to a specific size and shape by a common method.

Reaction conditions employed in the present invention are not specifically limited, and any reaction conditions commonly known to be useful for preparation of acrolein and methacrolein by gas-phase catalytic oxidation of propylene and isobutylene in a fixed-bed multi-tubular reactor can be employed.

The present invention also provides a catalyst for partial oxidation of propylene and isobutylene prepared according to the above process. The catalyst of the present invention shows higher conversion of propylene and isobutylene and shows high selectivity for partial oxidation of propylene and isobutylene, and can obtain acrolein and methacrolein with a high yield.

The present invention will be explained with reference to the following Examples. However, these are only to illustrate the present invention and the present invention is not limited to them.

EXAMPLE

Example 1

To a 500 cc glass reactor, 400 mL of distilled water were added, and heated to 75° C. while stirring. 300 g of citric acid were then added thereto and dissolved, and 100 g of ammonium molybdate, 39.4 g of ferrous nitrate, and 54.95 g of cobalt nitrate were sequentially added and completely dissolved. To the solution, a solution of 0.286 g of potassium nitrate and 34.35 g of bismuth nitrate in nitric acid was added, and the mixture was completely dissolved to prepare a catalyst suspension.

The thus-prepared catalyst suspension was dried in a microwave oven with a wavelength of 600 MHz for approximately 2 minutes for 10 ml of the catalyst suspension. The dried catalyst cake was recovered and pulverized to 40 mesh to prepare catalyst powders. The catalyst powders were collected, extruded in the form of cylindrical pellets, and calcined at 450° C. for hours in an air atmosphere to prepare a metal complex oxide catalyst with a composition of $Mo_{12}Bi_{1.5}Co_4Fe_2K_{0.06}$. The extrusion and calcining processes are applied in the same manner in the following Examples.

Example 2

To a 500 cc glass reactor, 400 mL of distilled water were added and heated to 75° C. while stirring. 200 g of citric acid were then added thereto and dissolved, and then 100 g of ammonium molybdate, 39.4 g of ferrous nitrate, and 60.44 g of cobalt nitrate were sequentially added and completely dissolved. To the solution, a solution of 34.35 g of bismuth and 0.286 g of potassium nitrate in nitric acid was added and completely dissolved to prepare a catalyst suspension.

The thus-prepared catalyst suspension was collected and dried in a microwave oven with a wavelength of 800 MHz for 30 seconds for 10 ml of the suspension. The dried catalyst cake was recovered and pulverized to 40 mesh to prepare catalyst powders. The catalyst powders were collected and calcined at 450° C. for 5 hours in an air atmosphere to prepare a metal complex oxide catalyst with a composition of $Mo_{12}Bi_{1.5}Co_{4.4}Fe_2K_{0.06}$.

Example 3

A metal complex oxide catalyst with a composition of $Mo_{12}Bi_{1.5}Co_{4.4}Fe_2K_{0.06}$ was prepared by the same method as in Example 2, except that a suspension was dried in microwave oven with a wavelength of 1 GHz for 30 seconds.

Example 4

A metal complex oxide catalyst with a composition of $Mo_{12}Bi_{1.5}Co_{4.4}Fe_2K_{0.06}$ was prepared by the same method as in Example 2, except that a suspension was prepared using 400 ml of nitric acid.

Example 5

A metal complex oxide catalyst with a composition of $Mo_{12}Bi_{1.5}Co_{4.4}Fe_2K_{0.06}$ was prepared by the same method as in Example 2, except that a suspension was prepared using 400 ml of water.

Comparative Example 1

To a 500 cc glass reactor, 400 mL of distilled water were added and heated to 75° C. while stirring. A solution of 100 g of ammonium molybdate, 39.4 g of ferrous nitrate, 60.44 g of cobalt nitrate, 34.35 g of bismuth nitrate, and 0.286 g of potassium nitrate in nitric acid was then added thereto to prepare a catalyst suspension.

100 mL of the prepared catalyst suspension were dried under vacuum. The dried cake was recovered and pulverized to 40 mesh to prepare catalyst powders. The catalyst powders were molded and calcined in a furnace at 450° C. for 5 hours to prepare a metal complex oxide catalyst with a composition of $Mo_{12}Bi_{1.5}Co_{4.4}Fe_2K_{0.06}$.

Experiment 1: Catalytic Activity Test

The catalysts prepared in Examples 1 to 3 and Comparative Example 1 were respectively charged into a reactor at 250~350° C. and 1~3 atmospheres. Then, 1~10 vol % of propylene, 1~15 vol % of oxygen, 5~60 vol % of vapor, and 20~80 vol % of inert gas were introduced on the catalyst with a space velocity of 500~2000 hours (STP). The propylene conversion rate, yield of acrolein and acrylic acid, and surface area of the catalyst were measured as follows, and the results are shown in Table 1.

a) propylene conversion rate—measured according to the following Equation 1.

Propylene conversion rate (%)=(moles of reacted propylene/moles of supplied propylene)×100     [Equation 1]

b) acrolein and acrylic acid yield—measured according to the following Equation 2.

Yield (%)=(moles of produced acrolein and acrylic acid/moles of supplied propylene)×100     [Equation 2]

c) surface area—measured by nitrogen adsorption method.

TABLE 1

|  | Example 1 | Example 2 | Example 3 |
|---|---|---|---|
| Drying method | microwave (600 MHZ) | microwave (800 MHZ) | microwave (1 GHZ) |
| Catalyst composition | $Mo_{12}Bi_{1.5}Co_4Fe_2K_{0.06}$ | $Mo_{12}Bi_{1.5}Co_4Fe_2K_{0.06}$ | $Mo_{12}Bi_{1.5}Co_4Fe_2K_{0.06}$ |
| Reaction temperature | 320° C. | 320° C. | 320° C. |
| Propylene Conversion rate (%) | 97.8 | 97.5 | 97.2 |
| Acrolein and acrylic acid yield (%) | 89.1 | 88.8 | 88.4 |
| Surface area (m²/g) | 17.5 | 16.8 | 14.3 |

|  | Example 4 | Example 5 | Comparative Example 1 |
|---|---|---|---|
| Drying method | microwave (800 MHZ) | microwave (800 MHZ) | Vacuum drying |
| Catalyst composition | $Mo_{12}Bi_{1.5}Co_4Fe_2K_{0.06}$ | $Mo_{12}Bi_{1.5}Co_4Fe_2K_{0.06}$ | $Mo_{12}Bi_{1.5}Co_{4.4}Fe_2K_{0.06}$ |

TABLE 1-continued

| | | | |
|---|---|---|---|
| Reaction temperature | 320° C. | 320° C. | 320° C. |
| Propylene Conversion rate (%) | 97.0 | 96.2 | 95.2 |
| Acrolein and acrylic acid yield (%) | 88.1 | 87.3 | 86.2 |
| Surface area (m²/g) | 12.4 | 9.4 | 5.7 |

As can be seen from the Table 1, the catalysts of Examples 1 to 5 prepared according to the present invention by drying in a microwave oven have superior propylene conversion rates, acrolein and acrylic acid yields, and surface areas, compared to the catalyst of Comparative Example 1.

The invention claimed is:

1. A process for preparing a catalyst for partial oxidation of propylene and iso-butylene represented by the following Chemical Formula 1, which process comprises the steps of:
   a) dissolving a metal salt compound comprising
      i) a molybdenum salt,
      ii) a bismuth salt,
      iii) an iron salt,
      iv) one or more salts of metals selected from the group consisting of cobalt, tungsten, vanadium, antimony, and nickel, and
      v) one or more salts of metals selected from the group consisting of potassium, rubidium, and cesium,
   in a nitric acid aqueous solution or in an organic acid solution to prepare a catalyst suspension;
   b) drying the catalyst suspension of step a) in a microwave oven;
   c) pulverizing and molding the dried catalyst of step b) to prepare a catalyst powder; and
   d) calcining the catalyst powder obtained in step c), $$Mo_aBi_bFe_cX_dY_eO_f \quad \text{[Chemical Formula 1]}$$

(wherein X is cobalt, tungsten, vanadium, antimony, or nickel, Y is potassium, rubidium, or cesium, each of a, b, c, d, and e represents the atomic mole ratio of each metal, and when a is 12, b is 0.5~2, c is 0.5~2, d is 3~8, and e is 0.005~0.2,
and f is determined according to oxidation state of each metal).

2. The process for preparing a catalyst for partial oxidation of propylene and iso-butylene according to claim 1, wherein the drying step b) comprises drying the solution in a microwave oven with a wavelength of 600 MHz to 2.5 GHz.

3. The process for preparing a catalyst for partial oxidation of propylene and iso-butylene according to claim 1, wherein the drying of step b) is carried out for 30 seconds to 5 minutes, for 10 mL of the catalyst suspension.

4. The process for preparing a catalyst for partial oxidation of propylene and iso-butylene according to claim 1, wherein the catalyst has a surface area of 10 to 20 m²/g.

5. A catalyst for partial oxidation of propylene and iso-butylene represented by the following Chemical Formula 1, which is prepared by the process of claim 1:

$$Mo_aBi_bFe_cX_dY_eO_f \quad \text{[Chemical Formula 1]}$$

(wherein X is cobalt, tungsten, vanadium, antimony, or nickel;
Y is potassium, rubidium, or cesium;
each of a, b, c, d, and e represents the atomic mole ratio of each metal, and when a is 12, b is 0.5~2, c is 0.5~2, d is 3~8, and e is 0.005~0.2; and f is
determined according to the oxidation state of each metal), wherein the catalyst has a surface area of 10 to 20 m²/g.

* * * * *